US005597714A

United States Patent [19]
Farone et al.

[11] Patent Number: 5,597,714
[45] Date of Patent: Jan. 28, 1997

[54] STRONG ACID HYDROLYSIS OF CELLULOSIC AND HEMICELLULOSIC MATERIALS

[75] Inventors: William A. Farone, Irvine; John E. Cuzens, Santa Ana, both of Calif.

[73] Assignee: Arkenol, Inc., Mission Viejo, Calif.

[21] Appl. No.: 483,455

[22] Filed: Jun. 7, 1995

Related U.S. Application Data

[63] Continuation-in-part of Ser. No. 38,628, Mar. 9, 1993, Pat. No. 5,326,701.

[51] Int. Cl.$^6$ .............. C13K 1/02; C12P 19/12; C12P 19/02; B01J 3/00
[52] U.S. Cl. .............. 435/100; 127/1; 127/36; 127/37; 127/46.2; 127/46.3; 210/665; 210/673; 536/1.11; 536/124; 536/127
[58] Field of Search .................. 127/1, 36, 37, 127/46.2, 46.3; 435/99, 100, 105, 16.1, 803, 168, 171, 921, 942, 911; 210/665, 673; 536/1.1, 124, 127, 127; 423/335, 339

[56] References Cited

U.S. PATENT DOCUMENTS

| | | |
|---|---|---|
| 4,242,455 | 12/1980 | Muller et al. . |
| 4,266,981 | 5/1981 | Tsao et al. . |
| 4,427,584 | 1/1984 | Legrand . |
| 4,556,430 | 12/1985 | Converse et al. . |
| 4,612,286 | 9/1986 | Sherman et al. . |
| 4,645,541 | 2/1987 | DeLong . |
| 4,668,340 | 5/1987 | Sherman . |
| 4,742,814 | 5/1988 | Sinner et al. . |
| 4,880,473 | 11/1989 | Scott et al. . |
| 5,084,104 | 1/1992 | Heikkila et al. . |
| 5,188,673 | 2/1993 | Clausen et al. . |

FOREIGN PATENT DOCUMENTS

| | | |
|---|---|---|
| 0035679 | 9/1981 | European Pat. Off. . |
| 0105937 | 4/1984 | European Pat. Off. . |
| 859449 | 8/1981 | U.S.S.R. . |

OTHER PUBLICATIONS

"The Butyl Alcohol-Isopropyl Alcohol Fermentation" Osburn, et al., *Journal of Biol. Chemistry.* 121:685-695 (1937).

"Studies on Anerobic Bacteria" Sjolander, *Journal Bacteriol,* 34:419-428 (1937).

"Kinetics of Wood Saccharification: Hydrolysis of Cellulose and Decomposition of Sugars in Dilute Acid at High Temperature".
Saeman, *Industrial and Engineering Chemistry,* 37: No. 1, pp. 43-52 (Jan. 1945).

"Factors affecting losses of sugars during acid hydrolysis of polysaccharides" LaBerge, et al., *LABP,* 19: No. 11, pp. 1121-1123 (Nov. 1970).

"Kinetics of the Acid Hydrolysis of Cellulose Found in Paper Refuse" Fagan, et al., *Environmental Science & Technology,* 5: No. 6, pp. 545-547 (Jun. 1971).

"Alcoholic Beverages" Rose, *Economic Microbiology,* 1:21-41 (1977).

"Comparison of the Economics of Acid and Enzymatic Hydrolysis of Newsprint" Grethlein, *Biotechnology and Bioengineering,* 20:503-525 (1978).

"Key Factors in the Hydrolysis of Cellulose" Saeman, *Symposium on Biomass as a Non-Fossil Fuel Source,* Presented Apr. 1-6, 1979, pp. 472-480.

"Rapid Ethanol Fermentation of Cellulose Hydrolysate" Ghose, et al., *Biotechnology and Bioengineering,* 21:1387-1400 (1979).

"Kinetics of Alcohol Fermentation at High Yeast Levels" (from Communications to the Editor) Rosario, et al., *Biotechnology and Bioengineering,* 21:1477-1482 (1979).

"Cellulose Degradation—A Common Link" Dunlap, et al., *Utilization and Recycle of Agricultural Wastes and Residues,* Chapter 2, pp. 19-65 (1980).

"The Production of Alcohol Fuels via Acid Hydrolysis Extrusion Technology" Noon, et al., Publication of Kansas Energy Office & Ozarks Commission, Revised May 1982.

"Characterization of Cellobiose Fermentations of Ethanol by Yeasts" Freer, et al., *Biotechnology and Bioengineering,* 25:541-557 (1983).

"Simultaneous Saccharification and Fermentation of Cellulose: Effect of Ethanol on Enzymatic Saccharification of Cellulose" Ooshima, et al., *Biotechnology and Bioengineering,* 27:389-397 (1985).

"Integrated Fuel Alcohol Production Systems, Phase III" Barrier, et al., Experimental Facility Testing Report for Jan. 15, 1984—Jan. 15, 1985.

"Integrated Fuel Alcohol Production Systems, Phase III" Barrier, et al., *Experimental Facility Testing Report,* Feb. 1985.

"Acid Hydrolysis Experimental Facility Results with Corn Stover" Barrier, et al., Jun. 23-26, 1985.

"Integrated Fuel Alhohol Production Systems, Phase III" Barrier, et al., Experimental Facility Testing Report for Jan. 15, 1985—Jan. 15, 1986.

"Integrated Production of Ethanol and Coproducts from Agricultural Biomass" Barrier, et al., Tennessee Valley Authority Biomass Program, (Apr. 1986).

"Silicon-based Materials from Rice Husk" Karera, et al., *Journal of Scientific & Industrial Research,* 45:441-448 (Oct. 1986).

"Process Considerations for Scale-up of Liquid Chromatography and Electrophoresis" Rudge, et al., *Separation, Recovery, and Purification in Biotechnology,* pp. 122-152 (1986).

(List continued on next page.)

*Primary Examiner*—Herbert J. Lilling
*Attorney, Agent, or Firm*—Knobbe, Martens, Olson & Bear

[57] ABSTRACT

A economically viable method for producing sugars using concentrated acid hydrolysis of biomass containing cellulose and hemicellulose is disclosed. The cellulose and hemicellulose in the biomass is first decrystallized and then hydrolyzed to produce a hydrolysate containing both sugars and acid. Silica and silicates present in the biomass can then be removed for further processing. The remaining solids are then subjected to a second decrystallization if necessary and a second hydrolyzation to optimize the sugar yields.

57 Claims, 3 Drawing Sheets

OTHER PUBLICATIONS

"Study of transformations of plant polysaccharides in the presence of acid catalysts" Rovenskii, et al., *Chemical Abstracts*, 109:104, cite 232958r (Dec. 19, 1988).

"Component composition and balance of hydrolysis products in carrying out cooking operations with the use of part of the hexose hydrolyzate on raw material loading" Popovtsev, et al., *Chemical Abstracts*, vol. 116, cite 8091q (Jan. 6, 1992).

"Application of Continuous Substrate Feeding to the ABE Fermentation: Relief of Product Inhibition Using Extraction, Perstraction, Stripping, and Pervaporation" Qureshi, et al., *Biotechnol. Prog.*, 8: No. 5, pp. 382–390 (1992).

STRONG ACID HYDROLYSIS OF CELLULOSIC AND HEMICELLULOSIC MATERIALS

RELATED APPLICATIONS

This application is a continuation-in-part of application Ser. No. 08/038,628, filed Mar. 26, 1993, U.S. Pat. No. 5,326,701.

FIELD OF THE INVENTION

The present invention relates to a process for hydrolysing biomass, and, more specifically, to a process for producing sugars through concentrated acid hydrolysis of materials containing cellulose and hemicellulose.

BACKGROUND OF THE INVENTION

Cellulose comprises the major part of all plant biomass. The source of all cellulose is the structural tissue of plants. It occurs in close association with hemicellulose and lignin, which together comprise the major components of plant fiber cells. Cellulose consists of long chains of beta glucosidic residues linked through the 1,4 positions. These linkages cause the cellulose to have a high crystallinity and thus a low accessibility to enzymes or acid catalysts. Hemicellulose is an amorphous hetero-polymer which is easily hydrolyzed. Lignin, an aromatic three-dimensional polymer, is interspersed among the cellulose and hemicellulose within the plant fiber cell.

It has been estimated that about three quarters of the approximately 24 million tons of biomass generated on cultivated lands and grasslands is waste. The utilization of such waste materials for developing alternate sources of fuels, chemicals and other useful products has long been desired. However, attempts to hydrolyze cellulose have not yet succeeded in providing an economically viable method for producing high yields of sugars, due primarily to the crystalline structure of cellulose and the presence of lignin therein.

Previously reported processes for hydrolysing cellulose include biological and non-biological means of depolymerization. The biological methods involve the use a cellulase enzyme. The oldest and best known non-biological method of producing sugars from cellulose is the use of acid hydrolysis. The acid most commonly used in this process is sulfuric acid. In general, sulfuric acid hydrolysis can be categorized as either dilute acid hydrolysis or concentrated acid hydrolysis.

The dilute acid processes generally involve the use of 0.5% to 15% sulfuric acid to hydrolyze the cellulosic material. In addition, temperatures ranging from 90°–600° Celsius, and pressure up to 800 psi are necessary to effect the hydrolysis. At high temperatures, the sugars degrade to form furfural and other undesirable byproducts. The resulting glucose yields are generally low, less than 50%. Accordingly, the dilute acid processes have not been successful in obtaining sugars from cellulosic material in high yields at low cost.

The concentrated acid processes have been somewhat more successful, producing higher yields of sugar. These processes typically involve the use of 60% to 90% sulfuric acid to effect hydrolysis. These processes, although successful at producing sugar yields above 90%, have not been implemented commercially in the past due to the high cost of concentrated sulfuric acid and its subsequent recovery, the difficulties encountered in handling concentrated sulfuric acid, and the need for equipment resistant to the acid at high temperatures. In addition, the higher the acid concentration used, the more energy required to concentrate the acid, resulting in these processes being economically disadvantageous.

More recently, however, the concentrated acid hydrolysis process has become the focus of additional research. (See L. T. Fan, M. M. Gharpuray and Y. H. Lee, Cellulose Hydrolysis, p. 170–172, 1992 and J. D. Broder, J. W. Barrier and G. R. Lightsey, "Conversion of Cotton Trash and Other Residues to Liquid Fuel", presented at the Conference of the American Society of Agricultural Engineers, Dec. 14–15, 1992.) Such processes generally consist of the following stages: (1) prehydrolysis to hydrolyze the hemicellulose portion, (2) main hydrolysis to hydrolyze the cellulose, and (3) post hydrolysis to form glucose from oligosaccharides formed in step (2). The first step involves the addition of sulfuric acid to the biomass which is then heated to at least 100° C. to break down the hemicellulose. The result of this prehydrolysis step is a solution containing not only virtually all of the $C_5$ sugars, but also $C_6$ sugars. These $C_6$ sugars are thus not recovered if the $C_5$ sugar stream is not utilized, resulting in lower sugar yields. After the sugar stream produced by the prehydrolysis step is removed, concentrated acid is added to disrupt the crystalline lattice of the cellulose and form glucose. The sugars produced are then fermented to alcohols. It has been recognized, however, that in order to commercialize such a process, the steps must be simplified, the energy consumption reduced, and the difficulties encountered in recycling spent acids eliminated.

Additional problems faced in the commercialization of known acid hydrolysis processes include the production of large amounts of gypsum when the spent or used acid is neutralized. The low sugar concentrations resulting from the processes require the need for concentration before fermentation can proceed. When hydrolysis is carried out at temperatures above 150° C., compounds such as furfural are produced from the degradation of pentoses. These compounds inhibit fermentation, and some are toxic.

In addition to these difficulties, it has been recognized that the fermentation of the sugars produced by concentrated acid hydrolysis presents additional problems. The hydrolysis of cellulose and hemicellulose results in the production of both $C_5$ and $C_6$ sugars. The hexose sugars are known to ferment easily, while the pentose sugars are generally more difficult to ferment. Thus, the resulting sugars must first be separated, which often involves the use of complicated separation techniques, and then fermented by different microorganisms known to ferment either hexose or pentose sugars alone.

Previous acid hydrolysis processes have not taken into account how biomass containing high amounts of silica are to be treated. Disposal of the silica poses a potential environmental and economic liability. In projects that use biomass to generate energy by combustion, high silica means high slagging tendency, as well as problems with handling large quantities of ash produced when the biomass is burned. Yet silicon compounds are of great commercial importance, and the recovery of silica from agricultural waste has become increasingly important. (See A. Karera, S. Nargis, S. Patel and M. Patel, "Silicon Based Materials from Rice Husk", Journal of Scientific & Industrial Research, Vol. 45, 1986, pp. 441–448.) It is well known that treatment of the biomass with sodium hydroxide will dissolve cellulose and hemicellulose, allowing their separation from the lignin. However, small chain cellulosics often contaminate the silica product during the removal process, thus lowering the sugar yield. In addition, the removal of the silica, done by filtration, is hampered by the formation of a thick gel which is very difficult to filter.

Thus, there is an urgent need for an economically viable, environmentally safe process for producing sugars from biomass containing cellulose and hemicellulose.

SUMMARY OF THE INVENTION

According to one aspect, the present invention provides a method of producing sugars from materials containing cellulose and hemicellulose. The materials are mixed with a solution of about 25–90% acid by weight to at least partially decrystallize the materials and form a gel that includes solid material and a liquid portion. The gel is diluted to an acid concentration of from about 20% to about 30% by weight and heated to a temperature between about 80° C. and 100° C. This effects a partial hydrolysis of the cellulose and hemicellulose contained in the starting materials. The liquid portion and the solid material are separated, thereby obtaining a first liquid containing sugars and acid. The separated solid material is mixed with a solution of about 25–90% acid until the acid concentration of the gel is between about 20–30% acid by weight and heated to a temperature between about 80° C. and 100° C. thereby further hydrolyzing the cellulose and hemicellulose remaining in the separated solid material and forming a second solid material and a second liquid portion. The second liquid portion is separated from the second solid material, thereby obtaining a second liquid containing sugars and acid. The first and second liquids are combined, and the sugars are separated from the acid in the combined first and second liquids to produce a third liquid containing a total of at least about 15% sugar by weight, which is not more than 3% acid by weight.

Preferably, the raw materials can be washed and dried to a moisture content of about 10% before processing. The materials can also be commuted to particles. Where the raw materials are of a density greater than about 0.3 gm/cc, the particles are of a size of about 0.075 mm to about 7 mm. Preferably, the particles are of an average size of about 5 mm. Where the raw materials are of a density less than about 0.3 gm/cc, the particles are of a size of about 0.075 mm to about 25 mm. Preferably, the particles are of an average size of about 15 mm. The commuting step can be performed by grinding, chopping or hammermilling.

The acid used can be selected from among hydrochloric acid, hydrofluoric acid, and phosphoric acid. Preferably, the acid used is sulfuric acid. The heating step is preferably performed for between 40 and 480 minutes. Specifically, the heating can be performed at a temperature of 100 degrees Celsius for 40–110 minutes, or at a temperature of 90 degrees Celsius for 80–220 minutes, or at a temperature of 80 degrees Celsius for 160 to 480 minutes. The hydrolysis is preferably performed at atmospheric pressure.

The gel and acid are preferably mixed at a speed of between about 10–30 rpm during hydrolysis. The acid used to effect decrystallization is preferably at a concentration of from about 70% to about 77% by weight, and the acid solution is added to achieve a ratio of pure acid to cellulosic and hemicellulosic material of at least about 1:1, more preferably about 1.25:1. Decrystallization is preferably performed at a temperature of less than 80° C., more preferably less than 60° C., and even more preferably, at a temperature between about 35°–40° C. The decrystallization step can further comprise the removal of heat using a vacuum to remove water which is recycled to the decrystallization step.

The method of the present invention is preferably performed using raw materials containing from about 50% to about 85% cellulose and hemicellulose, and at least 5% lignin. The separation of the liquid portion from the solid material is preferably performed by pressing the gel.

The second solid material can be pelletized to facilitate its further use.

In a preferred embodiment, the first and second liquid portions are combined before the separation of the sugars from the acid. The separation is performed using a resin separation unit wherein the sugars are adsorbed on a strong acid resin. Preferably, the resin separation unit is a cross-linked polystyrene cation exchange resin bed, and the resin is cross linked with divinylbenzene at a concentration of from about 6% to about 8% and treated with sulfuric acid to produce a strong acid resin. Alternatively, the resin is formed by polymerizing vinylbenzyl chloride with divinylbenzene at a concentration 6% to about 8% and treated with sodium sulfite to produce a strong acid resin. The resin is preferably in the form of beads having a diameter of from about 200 to about 500 micrometers, and the liquid preferably flows through the resin bed with an average linear flow rate of from about 2 to about 5 meters per hour. The resin bed can be heated to a temperature of from about 40 to about 60 degrees Celsius, and preferably has a tapped bed density of from about 0.6 g/ml to about 0.9 g/ml, and a strong acid capacity of at least about 2 meq/g.

The acid is preferably concentrated after the separation step for reuse.

In still another preferred embodiment of the method of the present invention, the mixing of the materials with the acid is performed in a vessel lined with a substance selected from the group consisting of polytetrafluoroethylene, polyvinylidene fluoride, a copolymer of chlorotrifluoroethylene and ethylene, high density polyethylene, polyvinyl chloride, and polypropylene. The decrystallization is preferably performed at a pressure of 150–400 mm Hg. The first mixing step preferably further comprises placing a portion of said materials in a reaction vessel, adding the acid, and gradually adding the remaining materials. The mixing steps are preferably performed using a multiple blade mixer.

In another preferred embodiment, the method of the present invention further comprises preparing the sugars for fermentation and fermenting the sugars to form fermentation products. The fermenting step comprises adjusting the pH of the sugars to neutralize any remaining acid and to remove metal ions, adding nutrients to allow growth of microbial organisms, mixing the sugars with a yeast selected from the group consisting of *Candida kefyr, Candida shehatae, Candida lignosa, Candida insectosa, Pichia stipitis,* respiratory deficient strains of *Saccharomyces cerevisiae, Hansenula anomala, Hansenula jadinii, Hansenula fabianii* and *Pachysolen tannophilus,* the yeast having been grown on pentose solutions for about 1 to 2 weeks, allowing the fermentation process to proceed to 3–5 days, continuously removing volatile fermentation products by recirculating carbon dioxide through a cooled condensing column, collecting the fermentation products from the condensing column, separating the yeast from the remaining fermentation products and distilling the remaining fermentation products. In one embodiment, the pH of the sugars is adjusted by adding a base until the pH reaches about 11, and then back titrating with acid to a pH of about 4.5.

In yet another preferred embodiment, the method of the present invention preferably further comprises treating the solid material with a metal hydroxide solution to produce an extract, reducing the pH of the extract to about pH 10 to produce silicic acid, and filtering the extract to remove said silicic acid. The metal hydroxide solution is preferably a solution of NaOH. The reducing is done with an acid such as sulfuric, hydrochloric, hydrofluoric, and phosphoric.

The silicic acid can be treated with an oxidizing agent to reduce the color of the silicic acid. The oxidizing agent is selected from among sodium hypochlorite, hydrogen peroxide, ozone, chlorine, and chlorine dioxide. The extract remaining after filtering is preferably neutralized before disposal. The silicic acid is preferably treated to produce silica gel, silicic acid and sodium silicate.

In a preferred embodiment, the metal hydroxide solution is a solution of sodium hydroxide, the reducing is done with sulfuric acid, and lime is added to the extract remaining after filtering to remove silicic acid to produce calcium sulfate and sodium hydroxide. The sodium hydroxide is then reused in treating step.

Further aspects of the present invention will become apparent to those of ordinary skill in the art upon reference to the ensuing description of the invention.

DETAILED DESCRIPTION OF THE INVENTION

Introduction

This invention provides an improved process for producing sugars from biomass containing cellulose and hemicellulose using concentrated acid, such as sulfuric, hydrochloric, hydrofluoric, or phosphoric acid. The sugars produced from this process can be used as animal or human food, as feedstock chemicals to make sugar derivatives such as sugar esters, or as feedstock for fermentation to ethanol or other products such as butanol, propanol, acetone, ethyl acetate, and many other chemicals for which specific microorganisms can be used to follow a specific metabolic pathway.

The process of the present invention provides a means for producing sugars from biomass which also reduces the amount of waste product or effluents produced. The process is designed to reuse all aqueous streams and to convert all solids to saleable or useful products. Much of the acid used is recovered for recycle. In the case where the biomass contains high levels of silica, the process is able to produce silica gel, sodium silicate, potassium silicate, zeolites, or other ancillary products. In the portions of the process involving fermentation, the fermentation of both the $C_5$ and $C_6$ sugars can be accomplished simultaneously using naturally occurring microorganisms. In addition, a high yield of sugar is obtained from the hydrolysis of the biomass, making concentration of the sugar streams prior to fermentation unnecessary.

Other features of the present invention that contribute to its efficiency and economic feasibility include the use of atmospheric pressure and relatively low temperatures. The process does not result in the production of furfural and similar undesirable by-products which are toxic and inhibit fermentation. The process of the present invention does not require the use of exotic and expensive materials of construction such as tantalum steel.

As will be explained more fully below, the process of the present invention provides an efficient, cost-effective means of producing useful chemicals from the hydrolysis of agricultural waste, while at the same time producing little or no waste effluents or materials.

The examples which follow are illustrative of the process of the present invention.

Decrystallization

Figure 1:
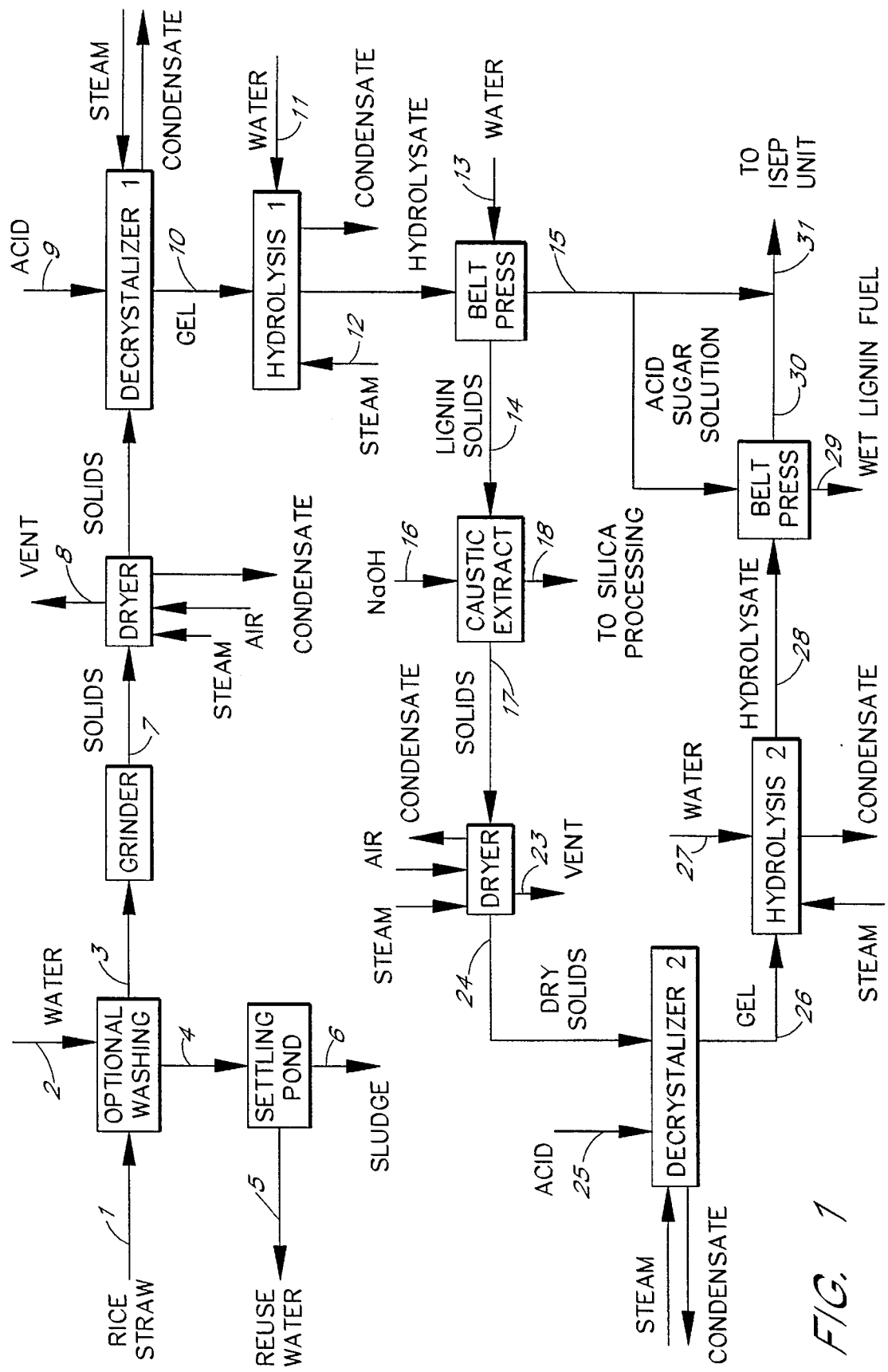
FIG. 1 is a schematic view of the method of the present invention, illustrating the decrystallization and hydrolysis stages.

The raw materials used in the method of the present invention are blended such that the cellulose and hemicellulose content is at least 65%, and more preferably about 75%. As an optional first step in the process, the biomass can be washed to remove gross dirt and contamination. As seen in FIG. 1, the rice straw 1, the biomass used as an example throughout the figures, is washed with water 2. In many instances, washing of the biomass is not necessary, as most "dirt" (clay, sand, small pieces of rocks) will pass through the process unchanged and end up in the lignin cake. Advantageously, the method of the present invention can be used with a variety of raw materials, including rice straw, which, because of its high silica content, is more difficult to process than other materials. It should be noted, however, that the principles of the present invention are not limited to any particular type of biomass, but are intended to apply to a broad range of materials. Rice straw is intended to be merely exemplary in nature.

After the washing is complete, the used water is transferred to a settling pond 4, to allow dirt and other sediment to collect on the bottom 6, after which the water can be reused 5 to wash the next portion of rice straw before processing.

Once the rice straw has been cleaned, it may be optionally dried 8, preferably to a moisture content of approximately 10%. After drying, the material is ground 7 into particles. For dense materials, that is, materials such as wood and rice straw having a density of greater than about 0.3 gm/cc, the particles should range in size from about 0.075 mm to 7 mm. Preferably, the particles range in size from 3 mm to 7 mm, and are of an average size of 5 mm. For materials having a density less than about 0.3 gm/cc, such as paper, particle size can be increased up to about 25 mm, with a preferred average size of 15 mm. It should be noted that for some materials the order of the drying and grinding steps should be reversed. That is, the material may be wet ground using a device such as a hydropulper and then dried.

The rice straw is now ready for the decrystallization stage. In the process of the present invention, raw materials containing cellulose and/or hemicellulose are first mixed with concentrated acid 9 at a concentration of between 25% and 90% to effect decrystallization. Preferably, the concentration of acid used is between 70% and 77%. Preferably, the acid used is sulfuric acid, but other acids including hydrochloric, hydrofluoric, and phosphoric acid are also contemplated. To reduce the occurrence of metal attack on the reaction chamber by the concentrated acid used, some of the biomass is placed in the reactor first, followed by the acid solution, followed by the gradual addition of the rest of the biomass. In addition, the reactor is preferably lined with thin layers of polytetrafluoroethylene (PTFE, known commercially as TEFLON), polyvinylidene (PVDF, known commercially as KYNAR), or a copolymer of chlorotrifluoroethylene (CTFE) and ethylene (known commercially as HALAR). High density polyethylene, polyvinyl chloride, and polypropylene can also be used.

The acid should be added to achieve a ratio of the weight of pure acid to the weight of cellulosic and hemicellulosic materials of at least 1:1. Preferably, the ratio achieved is 1.25:1. The addition of acid to the biomass results in the formation of a thick gel 10, having a viscosity of approximately 1.5 to 2 million cp, which is thoroughly mixed prior to hydrolysation. Advantageously, this mixture of the raw material with the acid results in the disruption of the bonds between the cellulose and hemicellulose chains, making the long chain cellulose available for hydrolysis.

The decrystallization is performed such that the temperature does not exceed 80° C., and is preferably in the range of 60°–80° C., or more preferably, the decrystallization should be below 60° C. with optimum results obtained when the cake is kept below a temperature of 35°–40° C. If the temperature during decrystallization exceeds 80° C., much of the $C_5$ sugars will be lost in the subsequent hydrolysis. The method of the present invention uses conditions which conserve the more reactive sugars that are produced earlier in the hydrolysis process. The decrystallization step prevents premature hydrolysis and consequently increased degradation of the sugars.

In the decrystallization step, the heat generated when large quantities of biomass and acid are mixed cannot be readily removed by conduction due to the low conductivity of the cake mixture. The removal under vacuum of water from the mixture, however, is sufficient to cool the mixture. The addition rate of the biomass, and thus the rate of the entire decrystallization process, is directly proportional to the rate at which water can be removed by the vacuum pump. The removal of water from the system by vacuum does not require the addition of solvent to remove the heat via evaporation, and the water, along with the small amount of acid entrained in the water, can be added back to the system after condensation, thus maintaining precise composition control and eliminating any waste product.

As the size of the reactor increases, the surface to volume ratio decreases. Since the decrystallization and hydrolysis material has very low thermal conductivity, the vacuum system removes an increasing percentage of the heat as the size of the reactor increases. In experiments performed in glass lined vessels the vacuum removed almost all of the heat due to the further decrease in the thermal conductivity of the glass. The vacuum also reacts much more rapidly than heat transfer through a surface.

The decrystallization stage is further described in Examples 1–3 which follow.

Example 1

Rice straw, containing 75% by weight of cellulose plus hemicellulose, and weighing 50.01 grams was mixed with 66.82 grams of 77% $H_2SO_4$. The rice straw was slowly added to the $H_2SO_4$ such that there was excess liquid available after each increment was added. The temperature was kept below 80° C. After the last amount of rice straw was added the resulting gelatinous mass was thoroughly mixed.

Example 2

Rice straw weighing 50.04 grams was mixed with 98.91 grams of 77% $H_2SO_4$. A small portion of the rice straw was placed in the reactor, the acid solution was added, and the remaining rice straw was slowly added to the $H_2SO_4$ such that there was excess liquid available after each increment was added. The temperature was kept below 80° C. by removing the water present in the mixture under vacuum. An initial pressure of 275 mm Hg (a vacuum of 757.26) was used to vaporize the solution at 40° C. Pressure of 180 mmHg (vacuum of 580 mm Hg) was sufficient to keep the solution cool at 40° C. After the last amount of rice straw was added the resulting gelatinous mass was thoroughly mixed.

Example 3

A mixture of wood prunings and newspaper weighing 100.00 grams was mixed with 167.63 grams of 77% $H_2SO_4$. The wood prunings were ground to 3–7 mm in size and 40 grams were mixed with 60 grams of the newspaper which had been shredded into approximately 6 mm pieces. The mixture was slowly added to the $H_2SO_4$ such that there was excess liquid available after each increment was added. The temperature was kept below 80° C. After the last amount of prunings and newspaper was added the resulting gelatinous mixture was thoroughly mixed.

First Hydrolysis

After the decrystallization stage, the concentrated acid in the mixture is diluted, preferably to a concentration of between 20% and 30%, and preferably using recycled water 11. This reduces the viscosity of the mixture from about 1.5 to 2 million cp to about 400,000 cp. The mixture is then heated to a temperature of between 80° and 100° Celsius and continuously mixed to effect hydrolysis 12. Mixing at low rotations per minute (rpm) is preferred, approximately 10–30 rpm. A second mixer at higher rpm is useful to keep the material in the vicinity of the slow speed mixer.

The hydrolysis is allowed to continue for between 40 and 480 minutes, depending on the temperature and the concentration of cellulose and hemicellulose in the raw materials. If the proper time is exceeded, the rate of degradation of the hexoses and pentoses will exceed their rate of formation. Thus, to increase the sugar yield, it is important to stop the first hydrolysis after a time and remove the sugars, then perform a second hydrolysis to convert the remainder of the cellulose and hemicellulose to sugars. After hydrolysis, the acid sugar solution is separated from the remaining solids, preferably by pressing 15, filtering, or filter pressing.

The filterability of the hydrolysate slurry is affected by the temperature at which the decrystallization takes place. The cooler the decrystallization can be kept the easier it is to filter the subsequent hydrolysis product. The decrystallization should be below 60° C. with optimum results obtained when the cake was kept below a temperature of 35°–40° C. It is impractical to keep it any cooler as the viscosity increases and the vacuum required to cool the mixture is too costly to maintain.

The benefit to filterability and higher yields from lower decrystallization temperatures indicates that the reactor design must be able to turn over the reacting materials and expose them to the lower pressure such that there is less than a 6° C. difference in temperature anywhere in the reactor. Multiple blade mixer designs are better suited to this than single blades.

Another way to ensure separability of the solids remaining after decrystallization and hydrolysis is to make sure the lignin present in the biomass is adequate to allow a filter press to be used to remove the sugar-acid solution after hydrolysis. If there is insufficient lignin present in the biomass and all of the cellulose and hemicellulose gets converted into sugars the solution will be very difficult to filter press. If the biomass was all cellulose and hemicellulose there would be no need to filter press as the sugar acid solution could go directly to the acid-sugar separation unit. However, whenever some of the biomass is not simply cellulose and hemicellulose it is desirable to have lignin present to act as an aid to filtering. In addition, the presence of lignin in the biomass also provides the following advantages: (1) it serves as a material upon which to deposit other materials such as inorganic materials and oxidized sugars; and (2) it acts as a co-product which can provide fuel value or be used as a media for growing plants or as a top soil additive.

It has been found that a combination of biomass materials with an average value of at least 5% lignin (dry basis) are best to assure enough cake is present to allow filtration. Lignin amounts of 7% are preferable as the best compromise between best filtration and optimal product yields. Higher amounts of lignin in the biomass make filtration even easier but the amount of sugars produced will be reduced because the additional lignin composition means less cellulose and hemicellulose will be available for hydrolysis.

The hydrolysis stage is further described in Examples 4–6 below.

Example 4

To the resulting gelatinous mass from Example 1, 54.67 grams of water were added for hydrolysis to reduce the acid concentration of the total mixture to 30%. The sample was heated to 100° C. for 60 minutes. Some water evaporation occurred during the heating. The gelatinous mass was pressed to yield 93 grams of a liquid which was 17.1% sugars and 35.52% acid.

Example 5

After the resulting gelatinous mass in Example 2 was thoroughly mixed, 104.56 grams of water were added to reduce the acid concentration of the total mixture to 30%. The sample was heated to 100° C. for 60 minutes. The gelatinous mass was pressed to yield 188.9 grams of a liquid which was 16.5% sugars and 34.23% acid.

Example 6

After the resulting gelatinous mass from Example 3 had been thoroughly mixed, 162.62 grams of water were added for hydrolysis to reduce the acid concentration of the total mixture to 30%. The sample was heated to 100° C. for 60 minutes. Some water evaporation occurred during the heating. The gelatinous mass was pressed to yield 214.3 grams of a liquid which was 17.6% sugars and 36.85% acid.

After pressing, the resulting cake containing the solid matter was washed with 170 grams of water and pressed again to yield a liquid which was 16.3% acid and 8.92% sugar, which was used for subsequent washing to increase the sugar yield.

Silica Processing

Figure 3:
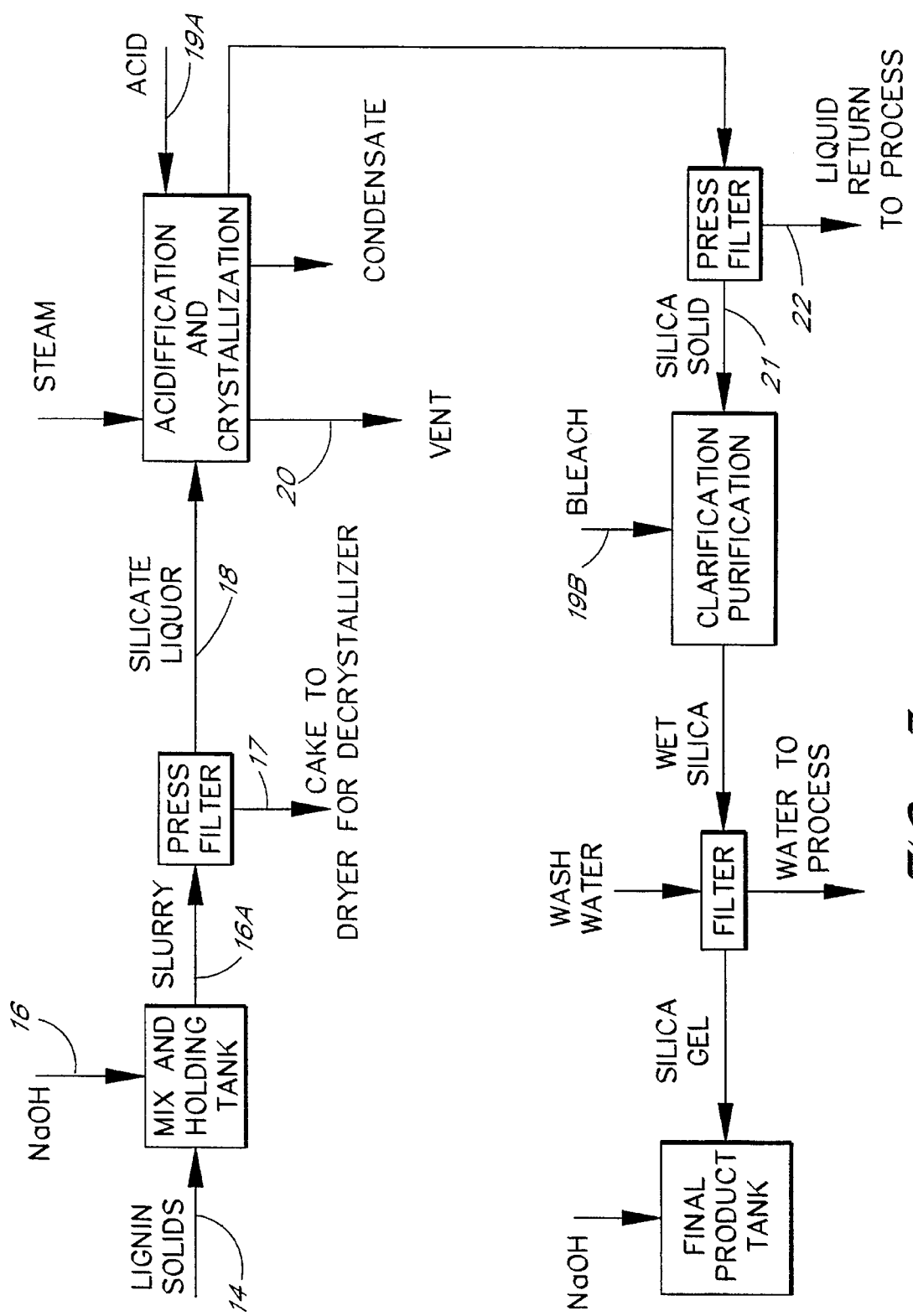
FIG. 3 is a schematic view of the method of the present invention, illustrating the silica processing stages.

The present invention advantageously also provides for the treatment of materials containing high amounts of silica. This process is illustrated in FIG. 3. The pressed solids 14 remaining after either the first hydrolysis or the second hydrolysis can be treated with a metal hydroxide solution, such as 5%–10% sodium hydroxide 16, in order to extract silicic acid 18. Preferably the metal hydroxide solution is a sodium hydroxide solution and is most preferably used at a concentration of about 8%. Longer times and higher temperatures give a higher yield of the product. However, for many biomass materials the lower conditions are adequate to produce silica in yields over 95% of theoretical recovery.

This stage of the process is optional, and is used when the biomass contains high amounts of silica, such as is the case with rice straw and cotton gin trash. After treatment with metal hydroxide solution 16 the solids are first heated 16A to approximately 60° C.–80° C. for about 60–90 minutes, and then filter pressed 17 and washed with water to extract a liquid 18. This liquid is treated with acid 19A to reduce the pH, creating a precipitate 21 which is separated, preferably by filtration 22. The acid used can be sulfuric, hydrochloric, hydrofluoric, or phosphoric. The material in the filter is bleached 19B to produce a material which is essentially pure silica gel. The oxidizing agent can be sodium hypochlorite, hydrogen peroxide, ozone, chlorine, or chlorine dioxide. This silica gel can be further treated to produce sodium silicate, potassium silicate, or other useful materials. For example, the silica can be mixed with aluminum salts, preferably aluminum sulfate, then washed and dried to form zeolites. The type of zeolite or silica produced is controlled by the amount of aluminum salt added and the impurities present in the silica as a result of processing. In other processes used to produce zeolites, a small amount of organic material is added to increase the "area", the sites available for absorption of chemicals, in the final crystal structure. In the process of the present invention, the normal impurities present in the biomass after hydrolysis act as the inorganic materials and a very high surface area material results. For example, zeolites made according to known methods using added aluminum salts have a Brunauer-Emmet-Teller (BET) surface area to nitrogen absorption of 150 $m^2$/gm for 17–19 micron particles. By using the method of the present invention, these levels can be obtained without the addition of aluminum salts, and 300–325 $m^2$/gm nitrogen absorption values can be obtained using aluminum salts.

When sulfuric acid has been used to hydrolyze the cellulosic and hemicellulosic materials, it is preferred to use sodium hydroxide solution as the metal hydroxide solution to extract silicic acid. The extraction of silica using sodium hydroxide makes sodium silicate solution which is filtered or pressed off the cake and then converted to silica by reaction with sulfuric acid. The reaction with sulfuric acid makes the desired silica product but also makes a sodium sulfate stream. The stream is treated with about 70% of the stoichiometric amount of lime (calcium hydroxide) needed to convert the sodium sulfate to calcium sulfate and regenerate much of the sodium hydroxide. Using higher amounts of lime does not significantly improve the yield of recovered sodium hydroxide.

The subsequently recycled stream of about 5% sodium hydroxide with portions of the remaining sodium sulfate is quite capable of continuing the silica extraction process and the remaining sodium sulfate does not interfere. The next and subsequent treatments with 5%–10% sodium hydroxide of the pressed solids remaining after the first or second hydrolysis can make use of the recycled sodium sulfate - sodium hydroxide solution.

The calcium sulfate (gypsum) product produced from the recovery of the sodium hydroxide can be combined with the calcium sulfate from the sugar product neutralization step to make an agricultural grade of gypsum.

The extraction of silica is further described in connection with Examples 7–10 below.

Example 7

Rice straw hydrolysis cake, formed as in Example 1 above, weighing 499.75 grams after pressing out the sugar hydrolysate was treated with 659.8 grams of 5% NaOH solution. The mixture was heated to 80° C. for 90 minutes. The cake was pressed and washed with water. The total liquid extracted was found to have a pH above 12. The liquid was treated with concentrated HCl to reduce the pH to 10. A light fluffy precipitate formed which was separated by filtration. The material was bleached in the filter by addition of 11% solution of NaOCl to produce an off-white material which is essentially pure silica gel. The material from the filter was recovered as silica by drying to the desired moisture level.

Example 8

The filter cake silica gel prepared by the method of Example 7 was treated with NaOH pellets to produce sodium silicate. Analysis of the sodium silicate solution by FT-IR spectroscopy showed recovery of the silica from the cake to be greater than 85%.

Example 9

The filter cake silica gel prepared by the method of Example 7 was treated with KOH pellets to produce potassium silicate in quantitative yields.

Example 10

Rice straw hydrolysis cake, formed as a result of the decrystallization and hydrolysis described above, weighing 206 pounds after pressing out the sugar hydrolysate was extracted with 352 pounds of a 5% NaOH solution. This mixture was filtered to produce 155 pounds of cake which is used for combustion or as soil compost. 403 pounds of liquid containing sodium silicate remained after filtration to remove the solids. 27 pounds of a 70% solution of sulfuric acid was added to the liquid to precipitate the silica, which was then filtered, producing 34 pounds of silica mixed with 44 pounds of water. The silica was washed with 10 pounds of hydrogen peroxide to bleach it. 396 pounds of liquid remained after filtration; this liquid contained 29 pounds of sodium sulfate. To this liquid was added 10 pounds of lime, and the resulting solution was stirred. After a few minutes, 73 pounds of calcium sulfate was filtered from the solution. The remaining liquid was a mixture of NaOH and $Na_2SO_4$ which was recycled and used for the next extraction procedure.

The 34 pounds of silica extracted as described above in 54 pounds of water was slurried with 0.4 pounds of aluminum sulfate. The mixture was rinsed with water and dried to produce 34.4 pounds of zeolites.

Second Decrystallization and Hydrolysis

To increase the sugar yields produced using the method of the present invention, yet another aspect of the present invention involves an optional second decrystallization and a second hydrolysis step. The second decrystallization step is unnecessary in most instances, however, for bulky materials such as wood, a second decrystallization step is performed when the first decrystallization step fails to adequately decrystallize the cellulosic and hemicellulosic materials.

The solids remaining after the first hydrolysis, or alternatively, the solids remaining after treatment with sodium hydroxide to extract silica, are dried 23. The dry solids 24 are mixed with concentrated sulfuric acid 25 at a concentration of between 25% and 90% to effect the second decrystallization, if necessary. Preferably, the acid concentration is between 70% and 77%. It is not necessary to hold the material for the same length of time as in the first decrystallization. In fact, this second decrystallization can be as short as the few minutes it takes to mix the acid and the solids. This second decrystallization also results in the formation of a thick gel 26.

The concentrated acid is then diluted, preferably to a concentration of between 20% and 30% and preferably using recycled water 27. The mixture is then heated to effect a second hydrolysis. Alternatively, in those cases where a second decrystallization is unnecessary, the solids remaining after the first hydrolysis, or after treatment to extract silica, are treated with 20–30% acid and heated to effect a second hydrolysis. The resulting gel 28 is pressed or filtered to obtain a second acid sugar stream 30, and the streams from the two hydrolysis steps are combined. The remaining lignin-rich solids are collected and optionally pelletized for fuel 29, or used as feedstock. Advantageously, pelletization of the lignin-rich cake helps reduce the waste produced by the process of the present invention.

Protein-type materials can be included as part of agricultural or waste materials used as feedstocks to the process of the present invention. Although sulfuric acid has been used to analyze for protein and amino acid nitrogen by releasing the nitrogen as ammonia (the so-called Kjeldahl test), there is no indication of ammonia release from protein in grasses and other plant materials in this process. This allows the use of products with protein without losing the nitrogen. The protein and amino acid nitrogen is still available, for example, as a natural nitrogen fertilizer, when the cake remaining after hydrolysation is used as a soil amendment. In addition, the nitrogen provides additional value to the lignin-rich cake as an animal food supplement.

The second decrystallization and hydrolysis steps are further explained in Examples 11 and 12 which follow.

Example 11

The cake formed from pressing after the first hydrolysis of rice straw was collected and dried to a moisture content of 10%. The cake, containing 41% cellulose and weighing 50.03 grams, was mixed with 33.28 grams of 77% $H_2SO_4$ to achieve a ratio of pure acid to cellulose of 1.25 to 1. The cake was slowly added to the acid and mixed until a thick gel was formed. The resulting pure acid concentration in the mixture was 30.75%, thus 17.00 grams of water was added to provide a final pure acid concentration of 25.5%. The mixture was then heated at 100° C. for 50 minutes. After cooling, the gel was pressed to recover 31.45 grams of a liquid containing 18.2% sugar and 21.1% acid. The cake containing the solids remaining after pressing was washed with 25 grams of water to produce a solution which was 15.4% sugar and 19.7% acid.

The pressed cake was dried to a water content of about 10%. This cake was shown to have a fuel value of 8,600 BTU per pound. This fuel material, which is primarily lignin with unrecovered sugar, some sugar degradation products, and some unreacted cellulose burned extremely well but left an ash that contained about 7% silica.

Example 12

The rice straw hydrolysis cake remaining after processing to remove silica, as explained in Example 7, which weighed 500 grams was mixed with 77% $H_2SO_4$ to achieve a ratio of pure acid to cellulose of 1.25 to 1. The cake was slowly added to the acid and mixed until a thick gel was formed. Water was then added to provide a final pure acid concentration of 25.5%. The mixture was then heated at 100° C. for 50 minutes. After cooling, the gel was pressed to recover a liquid containing both sugar and acid. The cake containing the solids remaining after pressing was washed with water to produce a second solution containing both sugar and acid.

The pressed cake was dried to a water content of about 10%. This cake was shown to have a fuel value of 8,600 BTU per pound. This fuel material, which is primarily lignin with unrecovered sugar, some sugar degradation products, and some unreacted cellulose burned extremely well and left an ash with a silica content of less than 1%.

Separation of Acid and Sugar

Figure 2:
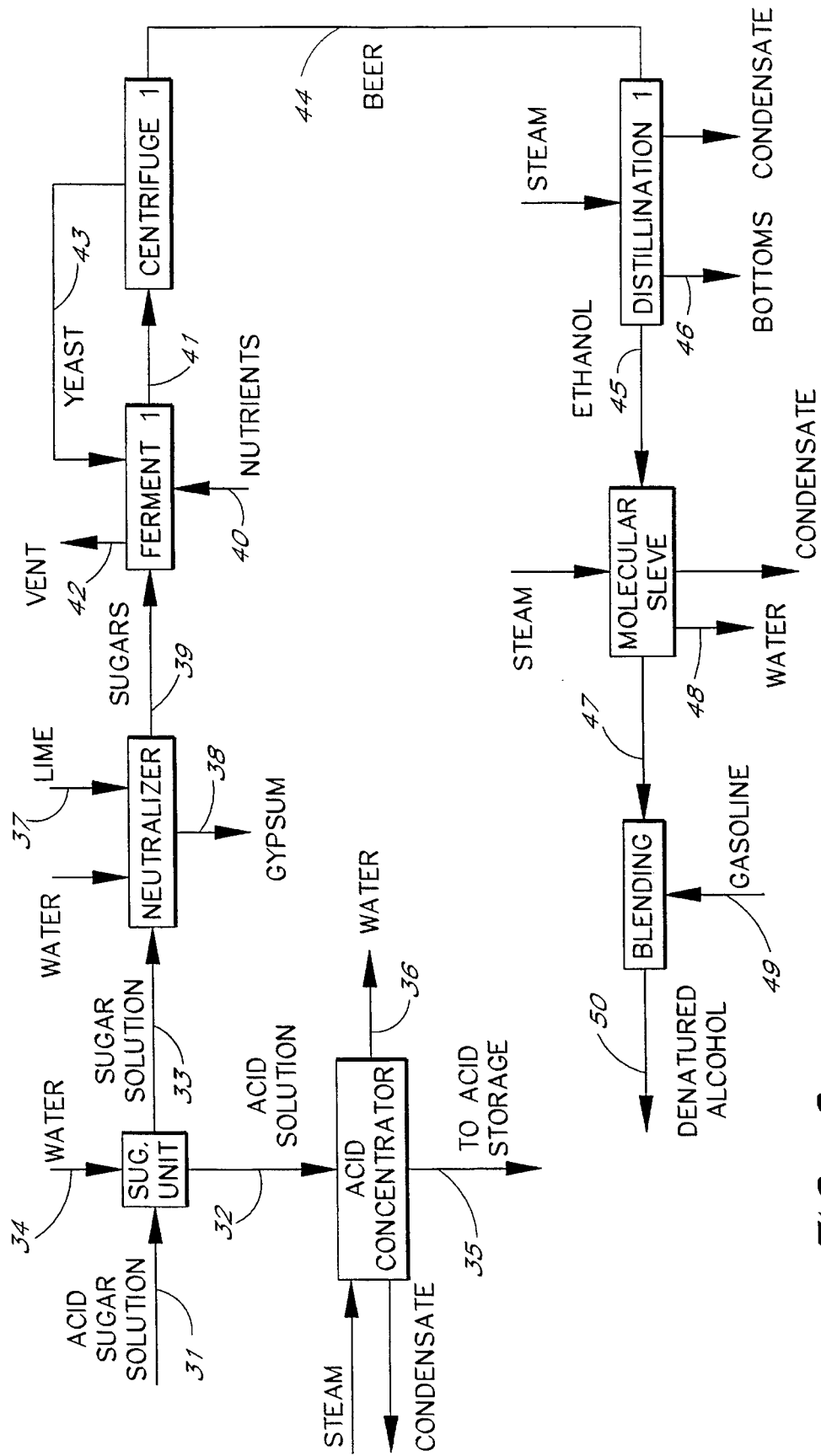
FIG. 2 is a schematic view of the method of the present invention, illustrating the separation, fermentation and acid reconcentration stages.

A further aspect of the present invention involves an improved method for separating the acid and sugar in the hydrolysate produced from the acid hydrolysis of cellulosic and hemicellulosic material. Referring now to FIG. 2, the acid sugar stream 31 is further processed through a separation unit, which comprises a strong acid polystyrene-divinylbenzene resin bed. The resin is preferably cross-linked with divinylbenzene, which is preferably at a concentration of between 6% and 8%, and treated with sulfuric acid such that it has a strong acid capacity of at least 2 meq/g. Several such resins are commercially available, including DOWEX 40166, available from Dow Chemical, Finex GS-16, available from Finex, Finland, Purolite PCR-771, available from Purolite Inc., Bala Cynwyd Pa., and IR-118, available from Rohm and Haas. In a particularly preferred embodiment, the resin used is DOW XFS 43281.01, available from Dow Chemical. The resin is preferably in the form of beads which are between 200 to 500 micrometers in diameter. The flow rate of the resin bed is preferably 2 to 5 meters per hour, and the bed preferably has a tapped bed density of between 0.6 and 0.9 g/ml. The resin bed should be heated, preferably to a temperature of between 40°–60° C. Higher temperatures can be used, but will result in premature degradation of the resin bed. Lower temperatures will result in separations which are not as effective.

The sugar is adsorbed on the column as the acid solution moves therethrough 32. Once the acid has eluted, the resin may optionally be purged with a gas which is substantially free of oxygen, preferably less than 0.1 ppm dissolved oxygen. This gas acts to push any remaining acid out of the resin, resulting in a cleaner separation.

After the elution of the acid stream, the resin is washed with water 34 that is substantially free of oxygen. The dissolved oxygen content of the water is preferably below 0.5 ppm, and more preferably, below 0.1 ppm. This washing results in the production of a sugar stream 33 containing at least 98% of the sugars in the hydrolysate that was added to the separation unit.

As a result of the separation process, three streams are collected: the acid stream, the sugar stream, and a mixed acid-sugar stream which is recycled through a second separation process. The acid stream 32 is reconcentrated and recycled for reuse, as will be explained more fully below. The sugar stream 33, which preferably contains at least 15% sugar and not more than 3% acid, can then be fermented, if desired. The purity of the sugar can be calculated as a percentage of the nonaqueous components of the sugar stream. Thus, any sugar purity of above 83.3% (100×15/18) is suitable for fermentation.

The inclusion of acid concentration as high as 3% in the sugar stream does not cause problems for further processing. However, loss of significant proportions of sugar with the acid upon separation can decrease the overall economy of the process.

In an exemplary, ideal separation process, 100 grams of water would be used to elute a 100 gram sample solution containing 30 grams of acid, 15 grams of sugar, and 55 grams of water from a separation column. In the case of perfect separation, the sugar stream would contain 15 grams of sugar and 85 grams of water. This would leave 30 grams of acid and 70 grams (100+55–85) of water for recovery of acid in the same concentration, 30%, as the original solution.

However, a typical elution for the 100 gram sample solution referred to above would require that about 200 grams of water be added to the column. The sugar stream is still 15%, but now the acid stream contains 170 grams (200+55–85) of water and 30 grams of acid, resulting in a 15% acid concentration. Thus, if the acid stream was 95% pure with an acid concentration of 15%, approximately 1.5 grams of sugar would be lost with the acid with every elution. If the sugar stream was 95% pure at a 15% concentration, only 0.75 grams of acid would be lost with every elution. This difference is due to the fact that the acid stream contains twice as much material. Thus, the purity of the acid stream is a more important factor than the purity of the sugar stream.

The separation of the acid and sugars is further explained in Examples 13–20 which follow.

Example 13

An acid sugar stream produced by the hydrolysis of cellulosic and hemicellulosic material was separated by flowing it through a 50 cm diameter glass column of 1.2 liters volume packed with PCR-771, a strong acid cation exchange resin available from Purolite, Inc. The column was held at 60° C. and the volumetric flow rate was 70 ml/min, which translates into a linear flow rate of about 0.8 meters per hour. Three streams were collected, the acid stream, the sugar stream and a mixed stream for recycle to another resin bed. The acid stream was 96.8% pure (sum of acid and water). The sugar stream was 86.8% pure (sum of sugar and water). Overall, the recovery of the acid was 97.3% and the recovery of the sugar was 95.5%.

Example 14

A portion of hydrolysate liquid produced by the acid hydrolysis of cellulosic and hemicellulosic material was separated by flowing it through a 50 cm diameter glass column of 1.2 liters volume packed with PCR-771, a strong acid cation exchange resin available from Purolite, Inc. The column was held at 40° C. and the volumetric flow rate was 70 ml/min. Three streams were collected, the acid stream, the sugar stream and a mixed stream for recycle to another resin bed. The acid stream was 95.1% pure (sum of acid and water). The sugar stream was 93.1% pure (sum of sugar and water). Overall, the recovery of the acid was 98.6% and the recovery of the sugar was 90.6%.

Example 15

A hydrolysis liquid containing 34.23% $H_2SO_4$ and 16.5% sugar was separated by flowing it through a 50 cm glass column of 1.2 liters volume packed with PCR-771, a strong acid cation exchange resin available from Purolite, Inc. The column was held at 60° C. and the volumetric flow rate was 70 ml/min. Three streams were collected, the acid stream, the sugar stream and a mixed stream for recycle to another resin bed. The acid stream was 96.47% pure (sum of acid and water). The sugar stream was 92.73% pure (sum of sugar and water). Overall, the recovery of the acid was 97.9% and the recovery of the sugar was 95.0%.

Example 16

Hydrolysate liquid produced from the hydrolysis of newspaper was found to contain 31.56% acid and 22.97% sugar. The liquid was separated by flowing it through a 50 cm glass column of 1.2 liters volume packed with PCR-771, a strong acid cation exchange resin available from Purolite, Inc. The column was held at 40° C. and the volumetric flow rate was 70 ml/min. Three streams were collected, the acid stream, the sugar stream and a mixed stream for recycle to another resin bed. The acid stream was 96.7% pure (sum of acid and water). The sugar stream was 90.9% pure (sum of sugar and water). Overall, the recovery of the acid was 99.5% and the recovery of the sugar was 96.7%.

Example 17

Hydrolysate liquid produced from the hydrolysis of newspaper was found to contain 31.56% acid and 22.97% sugar. A portion of the liquid was separated by flowing it through a 50 cm glass column of 1.2 liters volume packed with Finex GS-16, a strong acid cation exchange resin available from Finex, Finland. The column was held at 60° C. and the volumetric flow rate was 70 ml/min. A second portion of the liquid was also separated by flowing it through a 50 cm glass column of 1.2 liters volume packed with Finex GS-16. This column was held at 40° C. and the volumetric flow rate was 70 ml/min. In both cases, three streams were collected, the acid stream, the sugar stream and a mixed stream for recycle to another resin bed. The acid streams were at least 90% pure (sum of acid and water). The sugar streams were at least 94% pure (sum of sugar and water).

Example 18

A hydrolysate containing 15% sugar and 30% acid was separated using a 50 cm glass column of 1.2 liters volume packed with DOW XFS 43281.01 resin, available from Dow Chemical. The column was held at 60° C. and the volumetric flow rate was 65 ml/min. After adding the hydrolysate, the column was eluted with boiled and cooled distilled water. The acid stream was 97.0% pure, and the sugar stream was 97.2% pure. The amount of swelling between the acid and water phases on the resin was 2.48%.

A second addition of the same hydrolysate to the column followed by elution recovered essentially all of the acid and sugar, with over 99.1% recovery, and 97.2% sugar purity and 92.3% acid purity. The elution rate during the separation was 65 ml/min.

Example 19

An AST LC1000 rotating resin bed device manufactured by Advanced Separation Technologies, Inc. was used to separate the sugar-acid mixtures. The device consisted of 20 columns of resin, each column containing 2 liters of bed volume. The columns were filled with Finex GS-16 resin held at 60° C. In one run of 8 hours, the feed consisted of 14.89% sugar and 23.79% acid. The elution rate was 244 ml/min, which corresponds to linear rate of 0.12 m/min or 7.3 m/hour. The sugar product purity was 94.6% and the acid product purity was 92.4%. The sugar recovery was 84% with a concentration of 13.9%. The acid recovery was 97.5% with a concentration of 7.5%.

Example 20

An AST LC1000 rotating resin bed device manufactured by Advanced Separation Technologies, Inc. with a total bed volume of 15.2 liters was used to separate the sugar-acid mixtures. The columns were filled with Purolite PCR-771. The feed contained 12.6% sugar and 18.9% acid. The elution flow rate was 117 ml/min. The sugar purity in the recovered stream was 92.4% and the acid purity was 92.1% when the columns were operated at 60° C.

Upon analysis of the sugar mixture, it was determined that the distribution of sugars produced by the process of the present invention is remarkably consistent and consists primarily of 5 single C5 or C6 sugars; there is no evidence of dimer, trimer or other short chain polymeric sugars produced using this procedure. In addition, there is evidence, obtained, e.g., by gas chromatography of the trimethyl allyl esters, of the presence of xylitol in the C5 sugars. Xylitol is a reduced form of xylose and is easier for microorganisms to utilize.

Concentration and Recycling of Acid

The acid solution 32 recovered from the separation unit can be concentrated and recycled for reuse in the earlier stages of the process of the present invention. Concentration of the acid up to 35% is achieved through the use of a standard single stage evaporator 36. A triple effect evaporator, such as that available from Chemetics, Toronto, Ontario, Canada, is preferably used, resulting in increased concentrations of 70–77%. The water 35 recovered in the concentrator can be used as elution water in the resin separator unit.

Fermentation

Another aspect of the present invention involves an improved method for fermenting the sugar stream separated after the acid hydrolysis of cellulosic and hemicellulosic materials. The sugar stream contains both hexose and pentose sugars. These sugars can optionally be fermented simultaneously using naturally occurring microorganisms. Advantageously, this obviates the need for separation of the sugars, or their sequential fermentation.

The sugar solution 33 recovered from the separation unit after acid hydrolysis may still contain a residual amount of acid. This acid should first be neutralized 37, preferably with slaked lime, to a pH of between 10 and 12. This high pH advantageously removes all traces of metal ions that might interfere with subsequent processing. The solution is then back titrated with acid to a pH of about 4.5 Nutrients 40 such as magnesium, nitrogen, potassium phosphate and vitamins are then added to facilitate the growth of microorganisms. In addition, glucose oxidase can be added to the fermentation to assist in the process of conversion of xylose to ethanol.

One important aspect of the present invention is the ability to ferment both $C_5$ and $C_6$ sugars 39 together when desired. We have discovered that certain yeasts 43 cultured in a certain way are effective in this double fermentation. We have found that *Candida kefyr, C. shehatae, C. lignosa* and

*C. insectosa, Pichia stipitis*, and respiratory deficient strains of *Saccharomyces cerevisiae*, among others, work well at 25°–32° C., provided that they have been previously grown on pentose solutions for 1–2 weeks before being used on the mixed sugars.

If one desires to ferment the hexoses separately to recover the pentoses for other purposes, one can use known glucose yeasts such as *Saccharomyces cerevisiae*, and *Kluveromyces marxianus*. Certain bacteria also produce useful fermentation products and can be used in connection with the method of the present invention. The bacteria include Clostridium species and *Zymomonas mobilis*.

In cases where the yeast or bacterial fermentations slow down due to the repressing effects of ethanol or other volatile products, the volatile fermentation products can be removed continuously by recirculating the carbon dioxide produced by the fermentations through a cooled condensing column and then reintroducing the carbon dioxide into the fermenter. The volatile components, along with some water, condense in the column and can be collected for further purification. The process also has the advantageous effect of cooling the fermenter which is required for very active fermentations.

After the fermentation is complete, which takes approximately 3–5 days, the fermentation products and microorganisms are separated, preferably by centrifugation 41. The microorganisms 43 can be recycled to the next batch of sugars. The alcohol solution 44 can be sent to a distillation column 46 for further processing.

The preferred method of fermentation is further explained in Examples 21–22 which follow.

Example 21

Sugar solutions obtained from the resin separation columns over several runs were combined and neutralized with $Ca(OH)_2$ to pH 10 to 11. The solution was filtered to separate $CaSO_4$ (gypsum) and a clear yellowish sugar liquid. The pH of the sugar liquid was adjusted down to pH 4.5 by use of a combination of concentrated phosphoric acid and sulfuric acid. Phosphoric acid was added first to deliver 0.3 g/l of $H_3PO_4$. Nutrients were then added before the neutralization while the solution is still sterile due to the high pH. The nutrients included 0.07 g/l of $MgSO_4$, 0.2 g/l of $KNO_3$, 0.5 g/l of urea, 1.0 g/l of yeast extract, 0.1 mg/l of FeNaEDTA, 0.01 mg/l of $H_3BO_3$, 0.04 mg/l of $MnSO_4 \cdot H_2O$, 0.02 mg/l of $ZnSO_4 \cdot 7H_2O$, 0.003 g/l Kl, 1 µg/l of $Na_2MoO_4 \cdot 2H_2O$, 0.1 µg/l of $CuSO_4 \cdot 5H_2O$ and 0.1 µg/l of $CoCl_2 \cdot 6H_2O$.

The solution was then fed into a fermenter containing *Candida kefyr* (ATCC 8619), *Pichia stipitis* (NRRL Y-7124), *Hansenula anomala* (ATCC 42398), *Hansenula anomala* (ATCC 8168), *Hansenula fabianii* (ATCC 16755), *Hansenula jadinii* (ATCC 18201), or a respiratory deficient strain of *Saccharomyces cerevisiae*, which had been previously grown on 5% xylose media. The yeast "cream" in the fermenter contains at least 20 grams of yeast in approximately 100 ml of the 2 liter fermenter volume. Approximately 200 ml of the solution is added. The addition was repeated each day for three days. The yeast fermented both the C6 and C5 sugars in the solution.

Example 22

Sugar solutions obtained from the resin columns were combined and neutralized with $Ca(OH)_2$ to pH 10 to 11. The solution was filtered to separate $CaSO_4$ (gypsum) and a clear yellowish sugar liquid. The pH of the sugar liquid was adjusted down to pH 4.5 by use of a combination of concentrated phosphoric acid and sulfuric acid. Phosphoric acid is added first to deliver 0.35 g/l of $H_3PO_4$. Nutrients are added before the neutralization while the solution is still sterile due to the high pH. The nutrients included 0.07 g/l of $MgSO_4$, 0.2 g/l of $KNO_3$, 1.0 G/L OF $(NH_4)_2SO_4$, 1.0 g/l of yeast extract, 5.0 mg/l of $FeSO_4$, 1.0 mg/l of $H_3BO_3$, 5.0 mg/l of $MnSO_4 \cdot 2H_2O$, 10 µg/l of $CuSO_4 \cdot 4H_2O$, 20 µg/l of $COCl_2 \cdot 6H_2O$, 10 µg/l biotin, 0.25 mg/l pyridoxine HCl, 1.5 mg/l i-inositol, 2.0 mg/l Ca pantothenate, 5.0 mg/l thiamine HCl and 25 mg/l of peptone.

The solution was then fed into a fermenter containing *Candida kefyr* (ATCC 8619), *Pichia stipitis* (NRRL Y-7124), *Hansenula anomala* (ATCC 42398), *Hansenula anomala* (ATCC 8168), *Hansenula fabianii* (ATCC 16755), *Hansenula jadinii* (ATCC 18201), or a respiratory deficient strain of *Saccharomyces cerevisiae*, which had been previously grown on 5% xylose media. The yeast "cream," estimated to contain at least 20 grams of yeast, occupied approximately 100 ml of the 2 liter fermenter. Approximately 200 ml of the solution is added. The addition was repeated each day for three days. The yeast fermented both the C6 and C6 sugars in the solution.

The addition of $H_3BO_3$ to the media can be eliminated, if desired. $H_3BO_3$ should not be added to the media if bacteria, rather than yeasts, are used for fermentation, since boron is toxic to the bacteria.

Although certain examples have been used to illustrate and describe the present invention, it is intended that the scope of the invention not be limited to the specific examples set forth herein. Accordingly, the scope of the invention is intended to be defined only by the claims which follow.

What is claimed is:

1. A method of producing sugars from materials containing cellulose and hemicellulose comprising:

mixing the materials with a solution of about 25–90% acid by weight thereby at least partially decrystallizing the materials and forming a gel that includes solid material and a liquid portion;

diluting said gel to an acid concentration of from about 20% to about 30% by weight and heating said gel to a temperature between about 80° C. and 100° C. thereby partially hydrolyzing the cellulose and hemicellulose contained in said materials;

separating said liquid portion from said solid material, thereby obtaining a first liquid containing sugars and acid;

mixing the separated solid material with a solution of about 25–90% acid until the acid concentration of the gel is between about 20–30% acid by weight and heating the mixture to a temperature between about 80° C. and 100° C. thereby further hydrolyzing cellulose and hemicellulose remaining in said separated solid material and forming a second solid material and a second liquid portion;

separating said second liquid portion from said second solid material thereby obtaining a second liquid containing sugars and acid;

combining the first and second liquids; and separating the sugars from the acid in the combined first and second liquids by resin separation to produce a third liquid containing a total of at least about 15% sugar by weight, which is not more than 3% acid by weight.

2. The method of claim 1, further comprising washing said materials containing cellulose and hemicellulose.

3. The method of claim 1, further comprising drying said materials containing cellulose and hemicellulose.

4. The method of claim 3, wherein said materials are dried to a moisture content of about 10%.

5. The method of claim 1, further comprising commuting the materials containing cellulose and hemicellulose to particles.

6. The method of claim 5, wherein the materials are of a density of greater than about 0.3 gm/cc and said particles are of a size of about 0.075 mm to about 7 mm.

7. The method of claim 6, wherein the particles are of an average size of about 5 mm.

8. The method of claim 5, wherein the materials are of a density of less than about 0.3 gm/cc and said particles are of a size of about 0.075 mm to about 25 mm.

9. The method of claim 8, wherein the particles are of an average size of about 15 mm.

10. The method of claim 5, wherein the commuting step comprises a method selected from the group consisting of grinding, chopping and hammermilling.

11. The method of claim 1, wherein the acid is sulfuric acid.

12. The method of claim 1, wherein the acid is selected from the group consisting of hydrochloric acid, hydrofluoric acid and phosphoric acid.

13. The method of claim 1, wherein the heating is performed for between 40 and 480 minutes.

14. The method of claim 1, wherein the heating is performed at a temperature of 100 degrees Celsius for 40–110 minutes.

15. The method of claim 1, wherein the heating is performed at a temperature of 90 degrees Celsius for 80–220 minutes.

16. The method of claim 1, wherein the heating is performed at a temperature of 80 degrees Celsius for 160 to 480 minutes.

17. The method of claim 1, wherein the hydrolysis is performed at atmospheric pressure.

18. The method of claim 1, wherein the gel and acid are mixed at a speed of between about 10–30 rpm during hydrolysis.

19. The method of claim 1, wherein the acid used to effect decrystallization is at a concentration of from about 70% to about 77% by weight.

20. The method of claim 1, wherein the acid solution is added to achieve a ratio of pure acid to cellulosic and hemicellulosic material of at least about 1:1.

21. The method of claim 1, wherein the acid solution is added to achieve a ratio of pure acid to cellulosic and hemicellulosic material of about 1.25:1.

22. The method of claim 1, wherein the decrystallizing of the materials is performed at a temperature of less than 80° C.

23. The method of claim 1, wherein the decrystallizing of the materials is performed at a temperature of less than 60° C.

24. The method of claim 1, wherein the decrystallizing of the materials is performed at a temperature between about 35°–40° C.

25. The method of claim 1, wherein the decrystallization step further comprises removal of heat using a vacuum to remove water which is recycled to the decrystallization step.

26. The method of claim 1, wherein the raw materials contain from about 50% to about 85% cellulose and hemicellulose.

27. The method of claim 1, wherein the raw materials contain at least 5% lignin.

28. The method of claim 1, wherein the separation of the liquid portion from the solid material is performed by pressing the gel.

29. The method of claim 1, further comprising pelletizing the second solid material.

30. The method of claim 1, further comprising combining the first and second liquid portions before the separation of the sugars from the acid.

31. The method of claim 1, wherein the separation is performed using a resin separation unit wherein the sugars are adsorbed on a strong acid resin.

32. The method of claim 31, wherein the resin separation unit is a crosslinked polystyrene cation exchange resin bed.

33. The method of claim 31, wherein the resin is cross linked with divinylbenzene and treated with sulfuric acid to produce a strong acid resin.

34. The method of claim 33, wherein the divinylbenzene is at a concentration of from about 6% to about 8%.

35. The method of claim 31, wherein the resin is formed by polymerizing vinylbenzyl chloride with divinylbenzene and treated with sodium sulfite to produce a strong acid resin.

36. The method of claim 35, wherein the divinylbenzene is at a concentration of from about 6% to about 8%.

37. The method of claim 31, wherein the resin is in the form of beads having a diameter of from about 200 to about 500 micrometers.

38. The method of claim 32, wherein liquid flows through the resin bed with an average linear flow rate of from about 2 to about 5 meters per hour.

39. The method of claim 32, further comprising heating said resin bed to a temperature of from about 40 to about 60 degrees Celsius.

40. The method of claim 32, wherein the resin bed has a tapped bed density of from about 0.6 g/ml to about 0.9 g/ml.

41. The method of claim 31, wherein the resin has a strong acid capacity of at least about 2 meq/g.

42. The method of claim 1, further comprising concentrating the acid after the separation step for reuse.

43. The method of claim 1, wherein said mixing of the materials with the acid is performed in a vessel lined with a substance selected from the group consisting of polytetrafluoroethylene, polyvinylidene fluoride, a copolymer of chlorotrifluoroethylene and ethylene, high density polyethylene, polyvinyl chloride, and polypropylene.

44. The method of claim 1, the decrystallization is performed at a pressure of 150–400 mm Hg.

45. The method of claim 1, wherein said first mixing step further comprises placing a portion of said materials in a reaction vessel, adding the acid, and gradually adding the remaining materials.

46. The method of claim 1, wherein said mixing steps are performed using a multiple blade mixer.

47. The method of claim 1, further comprising preparing the sugars for fermentation and fermenting the sugars to form fermentation products.

48. The method of claim 47, wherein the fermenting step comprises:

adjusting the pH of the sugars to neutralize any remaining acid and to remove metal ions;

adding nutrients to allow growth of microbial organisms;

mixing the sugars with a yeast selected from the group consisting of *Candida kefyr, Candida shehatae, Candida lignosa, Candida insectosa, Pichia stipitis,* respiratory deficient strains of *Saccharomyces cerevisiae, Hansenula anomala, Hansenula jadinii, Hansenula fabianii* and *Pachysolen tannophilus,* said yeast having been grown on pentose solutions for about 1 to 2 weeks;

allowing the fermentation process to proceed to 3–5 days;

continuously removing volatile fermentation products by recirculating carbon dioxide through a cooled condensing column;

collecting the fermentation products from the condensing column;

separating the yeast from the remaining fermentation products; and distilling the remaining fermentation products.

49. The method of claim 48, wherein said pH of the sugars is adjusted by adding a base until the pH reaches about 11, and then back titrating with acid to a pH of about 4.5.

50. The method of claim 1, further comprising:

treating the solid material with a metal hydroxide solution to produce an extract;

reducing the pH of the extract to about pH 10 to produce silicic acid; and filtering said extract to remove said silicic acid.

51. The method of claim 50, wherein said metal hydroxide solution is a solution of sodium hydroxide.

52. The method of claim 50, wherein the reducing is done with an acid selected from the group consisting of sulfuric, hydrochloric, hydrofluoric, and phosphoric.

53. The method of claim 50, further comprising treating the silicic acid with an oxidizing agent to reduce the color of the silicic acid.

54. The method of claim 50, wherein the oxidizing agent is selected from the group consisting of sodium hypochlorite, hydrogen peroxide, ozone, chlorine, and chlorine dioxide.

55. The method of claim 50, further comprising neutralizing the extract remaining after filtering before disposal.

56. The method of claim 50, further comprising producing silica gel, silicic acid and sodium silicate from the silicic acid.

57. The method of claim 50, wherein the metal hydroxide solution is a solution of sodium hydroxide, wherein said reducing is done with sulfuric acid, and further comprising adding lime to the extract remaining after filtering to remove silicic acid to produce calcium sulfate and sodium hydroxide, and reusing said sodium hydroxide in said treating step.

* * * * *